United States Patent [19]

Inui

[11] Patent Number: 5,035,688
[45] Date of Patent: Jul. 30, 1991

[54] POLYP OR CELL BLOCK COLLECTING INSTRUMENT

[76] Inventor: Masahiko Inui, 909 Kamiyana Apt., 1-10-1 Kamiyama, Ichinomiya City, Aichi 491, Japan

[21] Appl. No.: 334,689

[22] Filed: Apr. 6, 1989

[51] Int. Cl.⁵ ............................................. A61M 5/00
[52] U.S. Cl. ..................................... 604/190; 604/319
[58] Field of Search ..................... 128/6, 758; 604/35, 604/118, 173, 190, 268, 319, 405, 406

[56] References Cited

U.S. PATENT DOCUMENTS

| | | | |
|---|---|---|---|
| 2,522,108 | 9/1950 | Flagg | 604/319 |
| 3,417,746 | 12/1968 | Moore et al. | 128/6 |
| 3,889,657 | 1/1975 | Baumgarten | 128/758 |
| 4,083,706 | 4/1978 | Wiley | 604/190 |
| 4,573,965 | 3/1986 | Russo | 604/35 |
| 4,615,694 | 10/1986 | Rarmes | 604/406 |
| 4,685,472 | 8/1987 | Muto | 604/190 |
| 4,813,931 | 3/1989 | Hauze | 604/319 |

*Primary Examiner*—Max Hindenburg
*Attorney, Agent, or Firm*—Kinney & Lange

[57] ABSTRACT

A polyp or cell block collecting instrument adapted for use with an endoscope having a suction passage. The instrument includes an upper stream tube section having a coupling end and a lower stream tube section having a coupling end removably coupled to the coupling end of the upper stream tube section. The coupling ends of the upper and lower stream tube sections have expanded diameter. A filter is mounted in the tube adjacent the coupling ends of the tube sections.

6 Claims, 2 Drawing Sheets

POLYP OR CELL BLOCK COLLECTING INSTRUMENT

BACKGROUND OF THE INVENTION

1. Field of the Invention

This invention is concerned with a polyp or cell block collecting device. In particular, the present invention is a collecting device used with an endoscope.

2. Description of the Prior Art

In medical treatment, when an endoscopic examination and especially a colon fiberscopic examination is conducted, the biopsy, polypectomy, erasion and collecting of a polyp is done under an endoscope to determine whether the cancer exists or not.

When this is carried out, sometimes the polyp is sucked from a suction hole on the top of an endoscope. After the polyp is sucked, it is placed in a suction bottle in which an enema, stool or wash are collected. It can be very difficult to find the polyp among the other collected substances. One technique is to filter the collected substances with gauze. This is unsanitary and produces a bad odor. There is also some danger of contamination or infection from a virus. Polyps and tissues collected by this method can also be damaged or degenerated to such an extent that they cannot be used as an examination specimen.

With collecting instruments currently used during an endoscope examination, the endoscope is usually taken out of the human body each time one polyp is collected. The insertion of an endoscope to the colon is done from the anus. When it is easy, it takes ten minutes. However, when it is difficult, it takes more than two hours, accompanied by pain to the patient. The examination has to be conducted to determine whether the polyp is benign or malignant. For diseases accompanied by colon polyps located in many places, frequent insertion of an endoscope into a human body to collect these polyps results in great pain to a patient and takes a long time. It is evident, therefore, that there is a continuing need for improved polyp collecting devices.

SUMMARY OF THE INVENTION

The present invention is a polyp or tissue collecting instrument adapted for use with an endoscope having a suction passage. The instrument includes a tube having an upstream end and a downstream end for connection to a suction passage of an endoscope. A filter is mounted in the tube. Polyps or tissues sucked through the suction passage of the endoscope are thereby collected.

In a preferred embodiment the tube includes an upper stream tube section having a coupling end and a lower stream tube section having a coupling end. The coupling ends of the tube sections are removably coupled to each other. The filter, which can include gauze, is positioned adjacent the coupling end of the upper or lower stream tube section. The coupling ends of the upper and lower stream tube sections can also have an expanded diameter.

DETAILED DESCRIPTION OF THE PREFERRED EMBODIMENTS

Figure 1:
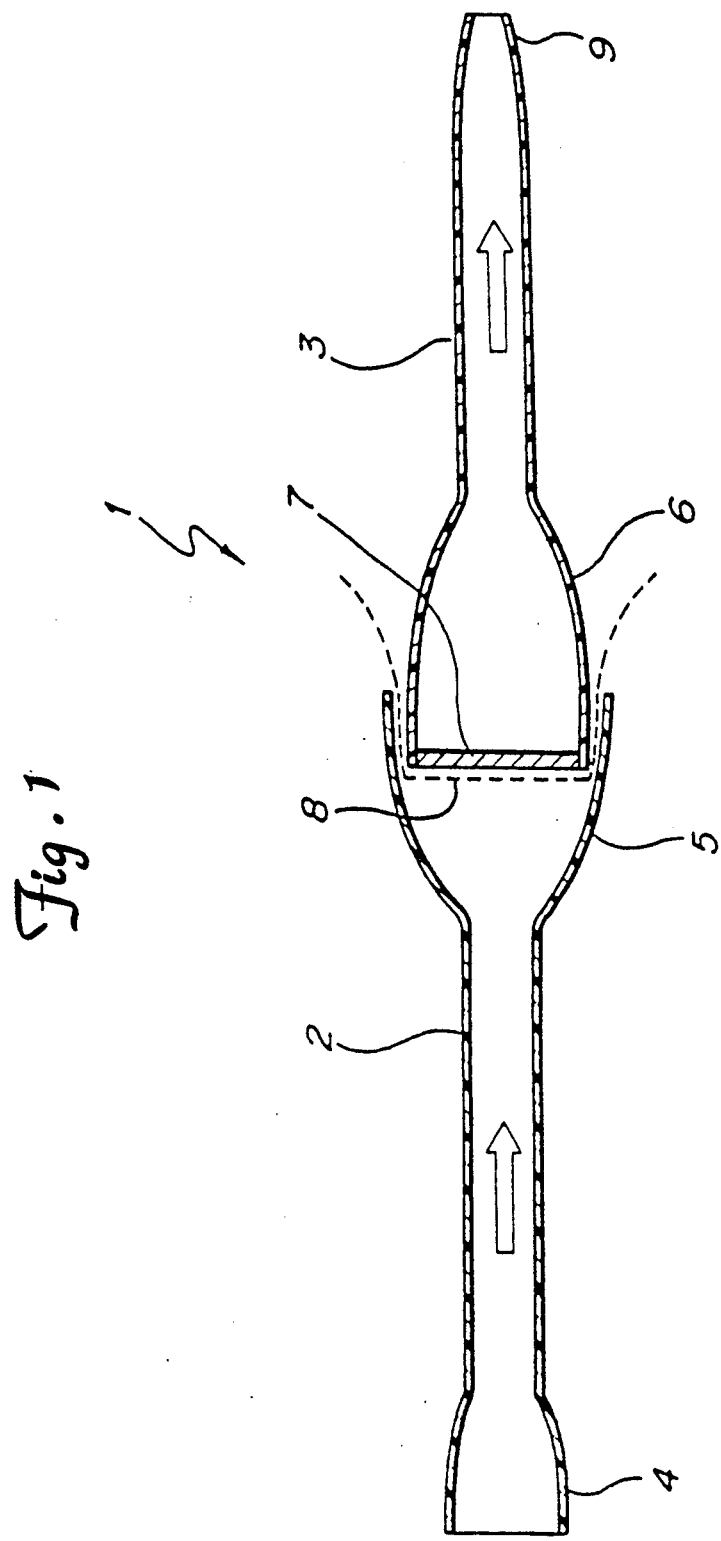
FIG. 1 is a cross section of a collecting instrument in accordance with the present invention.

As shown in FIG. 1, polyp or cell block collecting device 1 includes an upper stream tube 2 and a lower stream tube 3, and collects polyps at a coupling end of upper stream tube 2 and lower stream tube 3. Both upper stream tube 2 and lower stream tube 3 can be made of transparent material so that collected polyps can be easily detected. An upper stream edge of upper stream tube 2 is inserted into a suction passage of an endoscope (not shown) and has a slightly expanded receiving end 4 to prevent polyps from becoming entrapped. A lower stream edge of upper stream tube 2 is widely expanded to form deceleration chamber 5 which weakens the suction force and prevents the polyp from being destroyed. An upper stream edge of lower stream tube 3 is also widely expanded to permit insertion into deceleration chamber 5 of the lower edge of the upper stream tube 2, and forms coupling chamber 6. A surface of the upper stream edge of coupling chamber 6 is covered with washable net 7 having a stitch construction capable of blocking entrance of the polyps. A filter 8 which can be of the same material as net 7, such as gauze, can collect polyps against net 7, and make it possible to put a filter between an outer circumference of coupling chamber 6 of the lower stream edge and the inner circumference of deceleration chamber 5. The connecting portion of deceleration chamber 5 of lower stream tube 3 and coupling chamber 6 of upper stream tube 2 can be sealed hermetically to allow sufficient suction of the polyps. A lower stream edge of lower stream tube 3 is shaped to thrusting end 9 of a narrow diameter which can plug directly to the suction passage of an endoscope. Upper stream tube 2 and lower stream tube 3 can be made of plastic, glass or other materials. Either hard or soft materials can be chosen as the occasion demands.

Collecting instrument 1 is placed in a suction passage of an endoscope by inserting receiving end 4 of upper stream tube 2 and thrusting end 9 of lower stream tube 3, respectively. Polyps sucked from a suction hole of an endoscope point flow through receiving end 4 of upper stream tube 2, slow down at deceleration chamber 5 of the lower stream edge side of upper stream tube 2, and strike net 7 or filter 8. Deceleration chamber 5 of upper stream tube 2 and coupling chamber 6 of lower stream tube 3 can be disconnected to remove the polyp collected in net 7 or filter 8. A decision can be made whether to apply a new filter 8 to the side of coupling chamber 6 of lower stream tube 3 or not to use such a filter. In this manner, using a filter 8 such as gauze to which the polyps adhere, makes it easier to collect polyps and also takes less time.

Collecting instrument can be sealed hermetically by sealing the tube end of upper stream tube 2 to lower stream tube 3 with a sealing instrument made of metal or plastic. The collecting instrument 1 can then be used as a disposable device.

Use of collecting instrument 1 decreases chances of becoming contaminated or infected with bacteria or viruses compared with existing use of tweezers, etc. for collecting polyps directly for a pathological examination.

The tube end of upper stream tube 2 and lower stream tube 3 can be shaped to an inside diameter which can be inserted by an injection syringe, or constructed of a material which can be inserted by an injector needle. It can be used as a pathological examination container, and injected with a medical fluid such as formaldehyde. In this instance, a name, number or day of the week can be written with a pen, or a label with this identification information attached to the instrument, so that it can be used as a container for a pathological examination.

Figure 2:
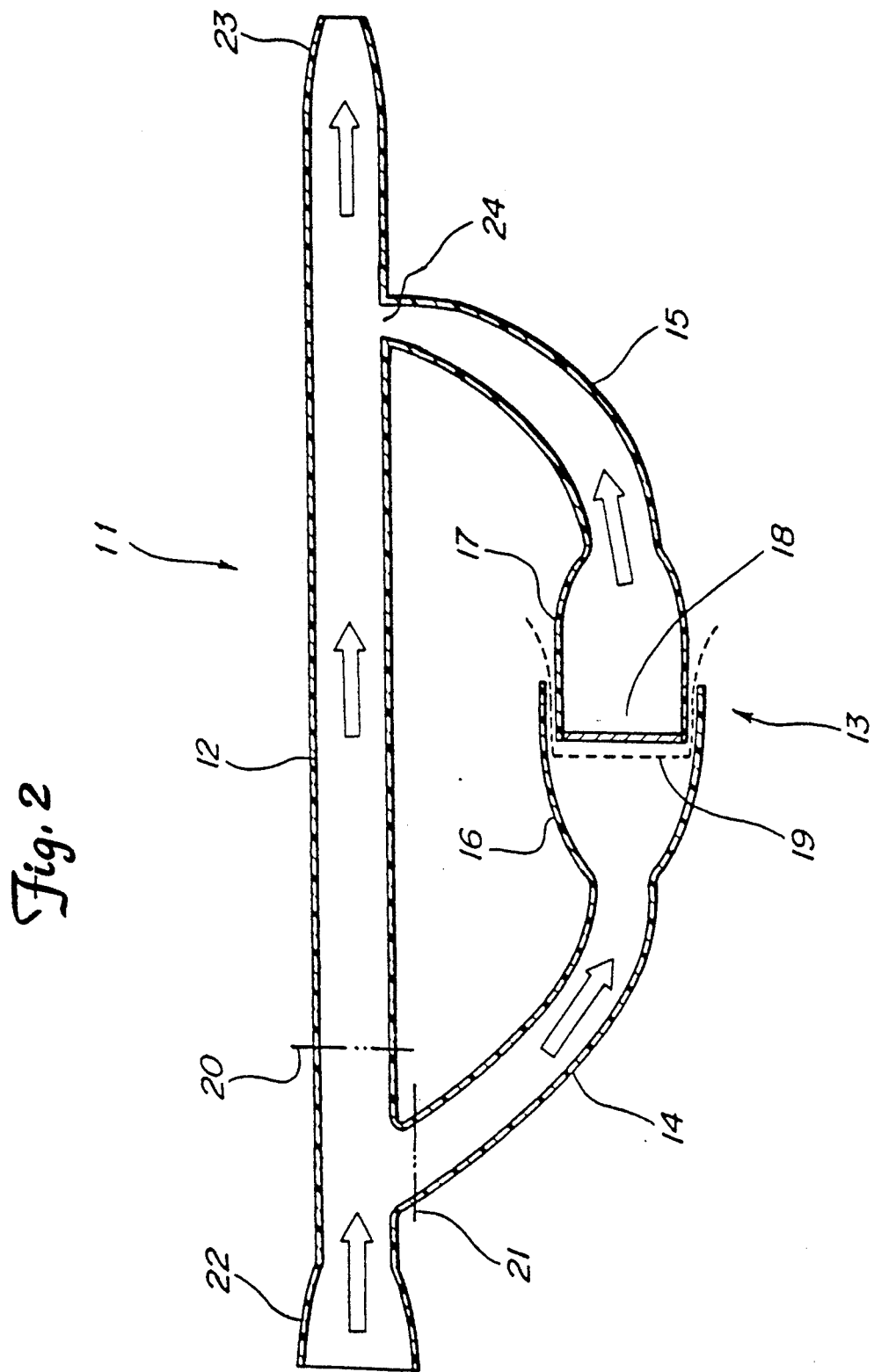
FIG. 2 is a cross section of a bypass tube collecting instrument in accordance with the present invention.

FIG. 2 shows a polyp or cell block collecting instrument 11 of a bypass type. This is made to be used to collect polyps, etc. without interruption of suction force necessary for an endoscopic examination.

Branch tube 13 which collects polyps and the like is attached to suction tube 12. Branch tube 13 includes an upper stream branch tube 14 and a lower stream branch tube 15. A lower stream edge of upper stream branch tube 14 is widely expanded to form deceleration chamber 16. An upper stream edge of lower stream branch tube 15 is inserted into deceleration chamber 16 to form coupling chamber 17, and an upper stream edge of coupling chamber 17 is covered with net 18. Gauze 19 can be applied to net 18 and placed between an outer circumference of coupling chamber 17 and an inner circumference of deceleration chamber 16. A connecting end of deceleration chamber 16 and coupling chamber 17 can be sealed hermetically. A three-way stop cock (not shown) can be inserted at a meeting point of suction tube 12 and upper stream branch tube 14. Alternatively clamps which close the stream passage at an intermediate lower stream end of the meeting point of suction tube 12 (indicated as 20) and at an intermediate lower stream end of the meeting point of upper stream branch tube 14 (indicated as 21) can be used. An upper stream edge of suction tube 12 forms receiving end 22 which is expanded. A lower stream edge is shaped as thrusting end 23 having a narrow diameter. Alternatively a clamp can be used. A connecting end of a lower stream edge of lower stream branch tube 15 and the lower stream edge of suction tube 12 makes a narrow diameter end 24 so as to avoid weakening of suction power of suction tube 12.

Collected polyps and the like can be made to flow into branch tube 13 by using the three-way stop cock or clamps. The collection of polyps can be carried out in a manner similar to that described above.

As described above, the collecting instrument of the present invention can be connected to a suction passage of an endoscope. There is no need to insert an endoscope many times into a body to remove polyps. If the polyp is small enough in size to pass through a suction passage of an endoscope, the polyp can be collected once the endoscope is inserted. Pain is thereby reduced as much as possible. Also, a specimen or polyp can easily be collected. As the polyp collecting instrument is set, being easily placed on or easily removed from a suction passage, it can be disposable thus decreasing the chances of infection caused by bacteria or viruses.

Although the present invention has been described with reference to preferred embodiments, workers skilled in the art will recognize that changes may be made in form and detail without departing from the spirit and scope of the invention.

What is claimed is:

1. A tissue collecting instrument adapted for use with an endoscope having a suction passage, including:
    an upper stream section having a suction passage connecting end configured for connection in the suction passage of an endoscope and having a collecting chamber portion of expanded diameter with a coupling end;
    a lower stream tube section having a suction passage connecting end configured for connection in the suction passage of an endoscope and having a collecting chamber portion of expanded diameter with a coupling end;
    a filter member fixedly mounted within and against the one of the collecting chamber portions of the upper and lower stream tube sections having a smaller diameter than the other; and
    the coupling end of the collecting chamber portion of the one of the upper and lower stream tube sections having the larger diameter being positioned against and about the coupling end of the other collecting chamber portion and also about the filter member therein.

2. A tissue collecting instrument adapted for use with an endoscope having a suction passage, including:
    an upper stream section having a suction passage connecting end configured for connection in the suction passage of an endoscope and having a collecting chamber portion of expanded diameter with a coupling end;
    a lower stream tube section having a suction passage connecting end configured for connection in the suction passage of an endoscope and having a collecting chamber portion of expanded diameter with a coupling end;
    a filter member fixedly mounted within the collecting chamber portion of the lower stream tube section and including a flexible filter member within the collecting chamber portions; and
    the coupling end of the collecting chamber portion of one of the upper and lower stream tube sections having a larger diameter than the other coupling end to enable the collecting chamber portion with the larger diameter coupling end to be frictionally engaged with the coupling end of the other collecting chamber portion with said flexible filter member having an edge secured between the frictionally engaged coupling ends of the collecting chamber portions.

3. The tissue collecting instrument of claim 2 wherein the flexible filter includes gauze material.

4. The tissue collecting instrument of claim 2 wherein the filter is adjacent the coupling end of the lower stream tube section.

5. A tissue collecting instrument adapted for use with an endoscope having a suction passage, including:
    an upper stream section having a suction passage connecting end configured for connection in the suction passage of an endoscope and having a collecting chamber portion of expanded diameter with a coupling end;
    a lower stream tube section having a suction passage connecting end configured for connection in the suction passage of an endoscope and having a collecting chamber portion of expanded diameter with a coupling end;
    a first filter member fixedly mounted within the collecting chamber portion of the lower stream tube section;
    the coupling end of the collecting chamber portion of one of the upper and lower stream tube sections having a larger diameter than the other coupling end to enable the collecting chamber portion with the larger diameter coupling end to be removably frictionally engaged with the coupling end of the other collecting chamber portion; and a second flexible filter member within the collecting chamber portions and having an edge secured between the frictionally engaged coupling ends of the collecting chamber portions.

6. The tissue collecting instrument of claim 5 wherein the second flexible filter member includes gauze material.

* * * * *

UNITED STATES PATENT AND TRADEMARK OFFICE
CERTIFICATE OF CORRECTION

PATENT NO. : 5,035,688
DATED : July 30, 1991
INVENTOR(S) : Masahiko Inui

It is certified that error appears in the above-identified patent and that said Letters Patent is hereby corrected as shown below:

On the title page insert the following:

[30]    Foreign Application Priority Data

Apr. 23, 1988  [JP]    Japan . . 63-54738

Signed and Sealed this

Twenty-second Day of December, 1992

*Attest:*

DOUGLAS B. COMER

*Attesting Officer*      *Acting Commissioner of Patents and Trademarks*